(12) United States Patent
Wyatt et al.

(10) Patent No.: US 6,368,349 B1
(45) Date of Patent: Apr. 9, 2002

(54) INFLATABLE NEURAL PROSTHESIS

(75) Inventors: John Wyatt, Sudbury, MA (US); Doug Shire, Ithaca, NY (US); Joseph Rizzo, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/717,738

(22) Filed: Nov. 21, 2000

(51) Int. Cl.[7] .................................................. A61F 2/16
(52) U.S. Cl. ........................................ 623/6.63; 607/54
(58) Field of Search ................................ 623/1.1–66.1; 607/54

(56) References Cited

U.S. PATENT DOCUMENTS 5,597,381 A * 1/1997 Rizzo, III ...................... 623/4
5,800,535 A * 9/1998 Howard, III ................. 607/118

* cited by examiner

Primary Examiner—Corrine McDermott
Assistant Examiner—Thomas Barrett
(74) Attorney, Agent, or Firm—Choate, Hall & Stewart

(57) ABSTRACT

Neural prosthesis for implantation within an eye. The prosthesis includes a foldable substrate and at least one electronic component supported by the substrate. At least one microchannel is disposed within the substrate. Upon inflation, the foldable substrate will unfold to provide for close contact of the electronic component with neural tissue, thus facilitating surgical implantation through a narrow incision, yet allowing the unfolded device to cover a sufficiently large portion of the patient's retina to provide useful vision.

13 Claims, 2 Drawing Sheets

INFLATABLE NEURAL PROSTHESIS

BACKGROUND OF THE INVENTION

This invention relates to a surgically implantable neural prosthesis and more particularly to a prosthesis which may be inserted into the eye in a folded state and later expanded to its operating state for contracting neural tissue such as the retina.

Tremendous societal benefits will result if some vision can be restored to patients who have become blind as a result of retinal disease such as age-related macular degeneration and retinitis pigmentosa. Macular degeneration affects 700,000 additional Americans each year and is the leading cause of blindness in the Western world. Retinitis pigmentosa, while less common, is the leading cause of inherited blindness and affects 1.6 million people worldwide. Both conditions are degenerative diseases of the outer retina. Macular degeneration primarily affects individuals near retirement age, whereas retinitis pigmentosa primarily affects younger adults. Macular degeneration causes loss of the central part of the visual field, making reading impossible. Retinitis pigmentosa initially causes gradual loss of peripheral vision, followed by loss of central vision resulting in total blindness. No effective preventative or cure is known for either disease.

These two diseases both arise from the anatomical problem of rod and cone degeneration. That is, in both diseases the rods and cones at the back of the retina degenerate, leaving the retina insensitive to light. The patient often becomes blind despite the retina retaining an active connection to the brain through a functioning optic nerve.

In the eye, the rod and cone photoreceptors are located far below the surface of the retina, while the ganglion cells and axons leading to the brain exist at the front of the retina. The ganglion cell layer lies only 20–40 microns from the retinal surface, and it can easily be stimulated by small currents from microelectrodes placed against or near the front retinal surface. See, U.S. Pat. No. 5,597,381. A goal of the retinal prosthesis of the invention is to electrically stimulate the retinal neurons to convey at least the outlines of a visual scene transmitted to the prosthesis as by an infrared laser, radio frequency source or other wireless techniques from outside the eye. An initial goal is thus to restore sufficient vision to blind patients to allow them to walk down a street unaided.

SUMMARY OF THE INVENTION

The neural prosthesis according to the invention includes a foldable substrate with a least one electronic component supported by the substrate. At least one air channel is disposed within the substrate. The electronic component may include an integrated circuit and/or an electrode array for stimulating neural tissue such as retinal tissue. It is preferred that the foldable substrate in an expanded state provides close apposition between the electrode array and the neural tissue.

In a preferred embodiment, the substrate includes a central region surrounded by projecting structures, each of the projecting structures including a microchannel. Each of the projecting structures includes the electrode array for stimulating neural tissue and the central region comprises power, control and driving circuits. The central region may be made of semiconducting material and the projecting structures made of a flexible insulating polymer which may contain polyimide. It is also preferred that the central region include a micromachined semiconducting nib through which a compressed gas or fluid can flow into the channel in each of the projecting structures.

Because the neural prosthesis of the invention includes a foldable substrate, the prosthesis can be inserted, for example, into the eye in a folded state through a relatively small surgical opening and once inside, inflated to an unfolded state to stimulate a relatively large area of neural tissue such as the retina. The prosthesis of the invention will also provide sufficient semiconductor area to implement the power, control and driving functions necessary for its operation.

DESCRIPTION OF THE PREFERRED EMBODIMENT

Figure 2:
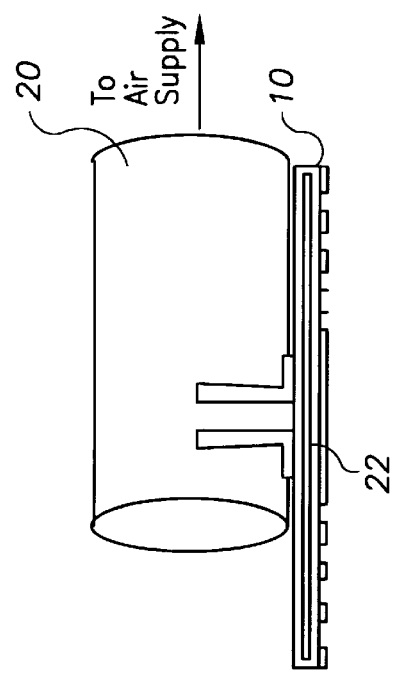
FIG. 2 is a cross-sectional view of a portion of the neural prosthesis of the invention.

As stated above, a goal of the present invention is to provide sufficient vision to blind patients to allow them to walk down a street unaided. Improved vision at this level depends more on having a sufficiently wide visual field than on the ability to resolve small objects or text with high acuity. For example, a visual field of 20 degrees corresponds to a 5 mm diameter disc on the retina. The insertion of such a relatively large implant to stimulate over a wide visual field would apparently require a large incision. It is well known, however, from, for example, cataract surgery that the eye tolerates small incisions much better than large ones. A wider device would apparently require a larger insertion wound which would increase the risk of infection, inflammation, and complications resulting from low intraocular pressure and vitreous loss. Once such a device has entered the eye, though, there is easily enough room to accommodate a width of 10 mm or wider. As will be discussed below, the prosthesis of the invention can stimulate a relatively large area of retina with a device that is inserted through a narrow incision only 2–3 mm wide.

The neural prosthesis of the invention requires significant semiconductor area within the eye for energy conversion, signal processing and electrode drive circuitry. Because the retina is only 0.3 mm thick and no stronger than one layer of wet facial tissue, silicon and other hard, standard semiconductor materials must be designed carefully for use within the eye. While it is possible to encapsulate a silicon chip in a soft, flexible material, the resulting structure tends to become massive enough to result in detrimental inertial loads on the retina during rapid eye motions and large enough to suffer fluid drag from vitreous motions within the eye. Thinning the silicon helps reduce mass and drag, but thinned silicon becomes quite sharp at the edges and can cut the retina unless it is heavily encapsulated. Thus, the prosthesis of the invention must have sufficient semiconductor area to perform the power, control and driving functions without cutting or dragging on the retina and should be insertable safely though a narrow incision.

The present invention reconciles the mutually opposing goals of having a relatively small ocular incision but a relatively large and flexible prosthesis with sufficient semiconductor area to implement the required electronics functions. The prosthesis of the invention is thus a microfabricated inflatable electronic device which is folded and then inserted into the eye in a collapsed state. Once inside the eye cavity the prosthesis is inflated to its full size. The prosthesis of the invention contains one or more thin semiconductor microchips which are interconnected by means of noble metal leads embedded in, for example, a flexible, waterproof insulating material. The metal leads may be gold suitably protected from the saline environment within the eye. Each semiconductor segment will be approximately 3 mm in diameter or less and thus the folded prosthesis structure will be able to pass through a narrow incision. The individual microchips making up the prosthesis are passivated with a biocompatible encapsulant such as a silicon carbide layer or a parylene film to protect the circuitry from the saline intraocular environment.

Figure 1:
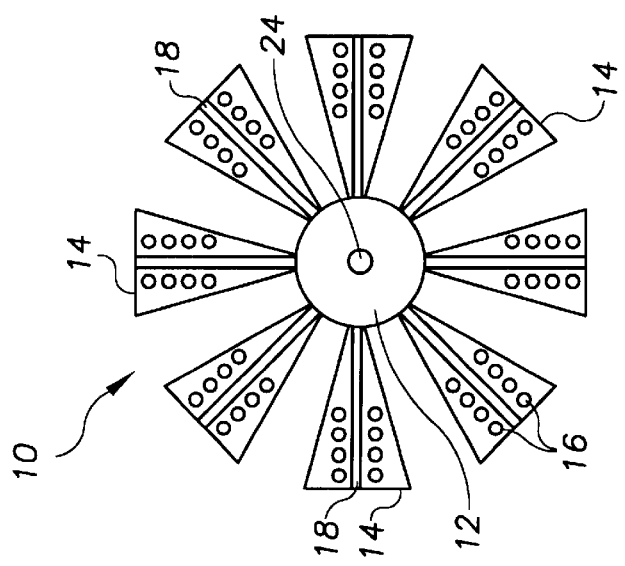
FIG. 1 is a plan view of the inflatable prosthesis of the invention.

With reference to FIG. 1, a neural prosthesis 10 is shown in its inflated or expanded state. The prosthesis 10 includes a central pod 12 with several tentacle-like extensions 14 radiating from the central pod 12. It is preferred that the extensions 14 be made of approximately 10-micron thick flexible insulating polymer that may include polyimide. The tentacle structure allows the prosthesis 10 to avoid buckling when it conforms, for example, to the spherical shape of the retinal surface (not shown). Further, the flexible insulating polymer material is extremely strong.

The tentacle-like extensions 14 include small microfabricated electrodes 16 embedded in the polyimide. Suitable electrodes 16 are made of activated iridium. The mechanical properties of the central pod 12 with extensions 14 enable a close apposition of the stimulating electrodes 16 to the neural tissue. The close apposition combined with the small microfabricated electrodes 16 embedded in the polyimide allow localized electrical fields to be used to induce finely detailed perception. These attributes will concomitantly reduce the amount of charge needed to stimulate the neural tissue, in turn reducing the potential for electrochemical toxicity. Without the extremely thin and flexible stimulating array within the extensions 14, the electrodes 16 cannot be in uniform contact with, for example the retina, which has a radius of curvature in the human of roughly 12 mm.

The prosthesis 10 will be folded for insertion into the eye through a surgical incision. In particular, the tentacle-like extensions 14 will be folded upwardly out of the plane of FIG. 1 resulting in an area substantially no bigger than the area of the central pod 12. Once inside the eye, the prosthesis 10 will be inflated to assume the state shown in FIG. 1. Inflation will be achieved using microchannels 18 fabricated inside the thin polymer extensions 14. The channels 18 will initially be made of polyimide and a sacrificial layer, for example of silicon dioxide, which is then overcoated with a second polyimide layer. The sacrificial layer is then dissolved in an appropriate chemical (such as hydrofluoric acid in the case of a sacrificial oxide) to create the hollow channels 18. After the prosthesis 10, in its folded state, has been introduced into the eye through a sclera incision, compressed air or other fluid will be used to inflate the implant to the state shown in FIG. 1. As shown in FIG. 2, air or other fluid will be injected via a semiconductor rubber tube 20 which will fit over a micro-machined semiconductor nib 22 on a surface of the central pod 12. This structure 22 will be etched into the backside of the silicon central pod 12 that bears the power, control and driving circuitry (not shown) for the prosthesis 10. A central hole 24 is etched all the way through the sacrificial layer that gives rise to the microchannels 18 prior to the dissolution referred to above. Once the sacrificial layer is dissolved the entire inflatable structure will be complete and ready for encapsulation and application to neural tissue such as a retina.

Depending on a particular design, it may be desirable to etch the microchannels 18 from both ends simultaneously rather than single-ended etching. The etching of the nib structure 22 can involve a multiple-step etching in a Bosch process rapid silicon etching system along with conventional RIE tools. An appropriate masking material and end point indicator will be necessary to create this structure. It is preferred that the silicone tube 20 be attached to the prosthesis 10 by means of a V-groove (not shown) into which the tubing will be laid parallel to the front silicon surface on the prosthesis 10 as shown in FIG. 2. A small hole (not shown) in a side of the tube 20 fits over the micromachined semiconductor nib 22.

In use, the prosthesis 10 in its folded up configuration will be inserted into the eye through a small incision. When air or other fluid of sufficient pressure is introduced into the prosthesis 10, it will unfurl and assume the flat shape shown in FIG. 1. The amount of gas or fluid added to the prosthesis 10 can be varied allowing a surgeon or other individual using the device to alter the rigidity or location of the prosthesis. For example, if the surgeon inflates the prosthesis, and he or she determines that the prosthesis should be repositioned, some or all of the air or fluid used to inflate the prosthesis can be removed. If some of the air or fluid remains in at least one of the extensions 14, when additional air or fluid is reintroduced into the remaining extensions, the extensions will perform like small legs slightly changing the position of the prosthesis 10. In this way, a surgeon would be capable of precisely locating the prosthesis 10 of the present invention. Similarly, if the surgeon desired to reduce or increase the rigidity of the present invention, simply adding or removing a portion of the gas or fluid used to inflate the prosthesis 10 would accomplish this result.

Excessive air pressure must be avoided so that the prosthesis 10 does not come apart. It is necessary that the inflatable implant assume its flat shape only for a period of approximately one hour, since it will be affixed to the retinal surface and the silicone tube 20 cut off at the conclusion of the surgery. The prosthesis 10 may be affixed to the retinal surface by any suitable technique such as with the use of a light-activated polymer or the use of retinal tacks.

Figure 3:
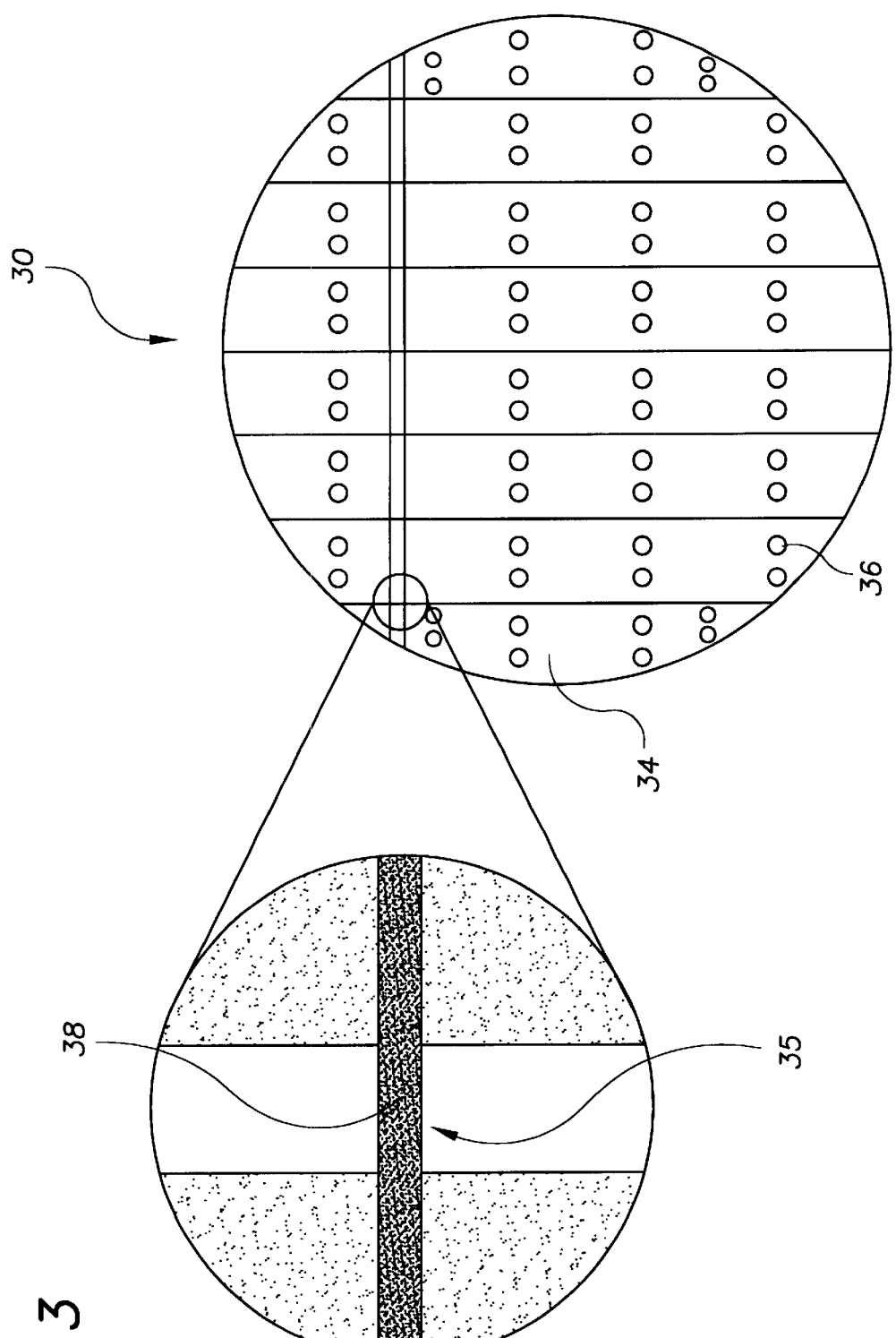
FIG. 3 is a plan view of an alternate embodiment of the inflatable prosthesis of the invention.

In an alternate embodiment, a prosthesis 30 may be constructed as shown in FIG. 3. The neural prosthesis 30 of FIG. 3 is shown in its inflated or expanded state. The structure and composition of the alternate embodiment are similar to that described with reference to the preferred embodiment of FIG. 1, except that the alternate embodiment differs in the following ways. Before being passed through an incision in the eye in this alternate embodiment, the sections 34 of the prosthesis 30 are folded over each other, much like the blades of a paper fan before it is opened. The sections 34 of the alternate embodiment are secured to one another via a supporting structure 35, such as hinges. Channels 38, through which the gas or fluid used to inflate the sections 34 once the prosthesis has been placed inside the incision in the eye, run through the supporting structures 35. As was the case with the tentacle-like extensions 14 of FIG. 1, each section 34 in the alternate embodiment of FIG. 3 includes small microfabricated electrodes 36. In this embodiment, the width of each section 34 could be approximately 3 mm or less. The incision used in this embodiment is likely, therefore, to be as small as that described above with reference to FIG. 1. In addition, once the prosthesis 34 of this embodiment is passed through the incision into the eye, compressed gas or fluid can be used, as was described above, to inflate the sections 34 of the prosthesis, thereby unfolding each section 34 so that the prosthesis 30 is then ready for encapsulation and application to the retina.

The neural prosthesis design disclosed herein allows the permanent placement of a microelectrode array near the retinal neurons without mechanical harm to the delicate retina. By using a wireless system such as an infrared laser or RF source to transmit power and visual data to an appropriate receiver within the implanted prosthesis, chronic penetration of the surface of the eye is avoided. The use of biocompatible materials and sufficiently low currents substantially avoids chemical and electrochemical toxicity. Effective encapsulation of the implanted circuitry will protect it from the saline fluids within the eye. The prosthesis of the invention will process video data about the patient's environment transmitted to it from an external camera and retransmit this data to the activated iridium electrode array 16 to provide useful visual perception, and the tentacle-like extensions 14 allow for sufficient nutrient flow to the underlying retinal tissue to assure its continued health. Finally, the design of the present invention allows it to be inserted through a narrow incision in the sclera.

It is recognized that modifications and variations of the present invention will be apparent to those skilled in the art. All such modifications and variations are included within the scope of the appended claims.

What is claimed is:

1. Neural prosthesis comprising:
   a foldable substrate;
   at least one electronic component supported by the substrate; and
   at least one microchannel disposed within the substrate for expanding the substrate.

2. The neural prosthesis of claim 1 wherein the electronic component is an integrated circuit.

3. The neural prosthesis of claim 1 wherein the electronic component is an electrode array.

4. The neural prosthesis of claim 3 wherein the foldable substrate in an expanded state provides close apposition between the electrode array and neural tissue within the eye.

5. The neural prosthesis of claim 1 wherein the substrate includes a central region surrounded by projecting structures, each of the projecting structures including the microchannel.

6. The neural prosthesis of claim 5 wherein the projecting structures include an electrode array for stimulating neural tissue.

7. The neural prosthesis of claim 5 wherein the central region comprises silicon and the projecting structures comprise a flexible insulating polymer.

8. The neural prosthesis of claim 3 wherein the electrode array includes activated iridium electrodes.

9. The neural prosthesis of claim 5 wherein the central region includes structure for attaching a source of pressurized gas or fluid for inflating the prosthesis.

10. The neural prosthesis of claim 9 wherein the source of pressurized gas or fluid includes means for altering the position of the prosthesis.

11. The neural prosthesis of claim 9 wherein the source of pressurized gas or fluid includes means for altering the degree of inflation of the prosthesis.

12. The neural prosthesis of claim 1 wherein the foldable substrate includes structure for attaching a source of pressurized gas or fluid for inflating the prosthesis.

13. The neural prosthesis of claim 1 wherein the substrate includes multiple foldable sections.

* * * * *